Figure 1:
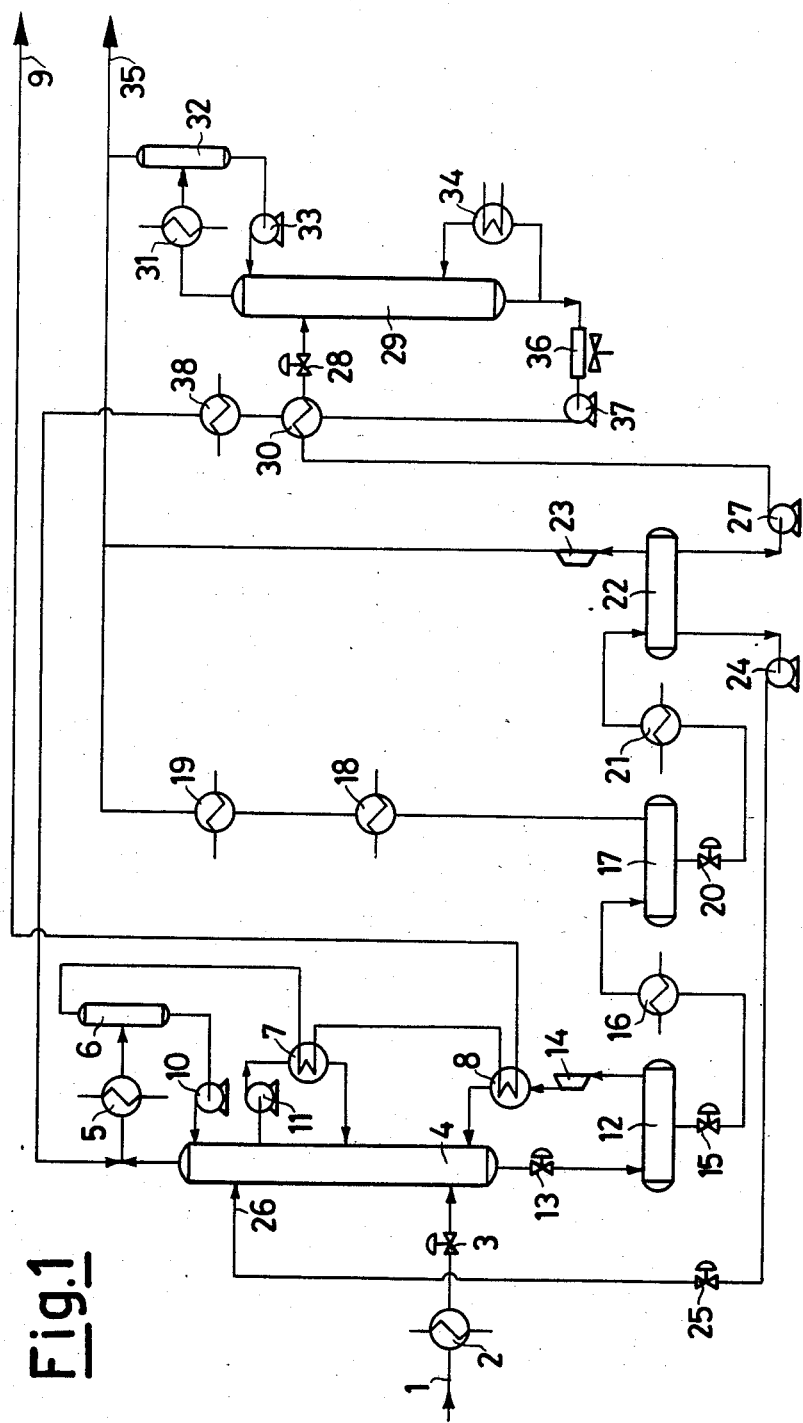

United States Patent [19]

Gazzi et al.

[11] Patent Number: 4,591,370
[45] Date of Patent: * May 27, 1986

[54] CRYOGENIC PROCESS FOR REMOVING ACID GASES FROM GAS MIXTURES BY MEANS OF A SOLVENT

[75] Inventors: Luigi Gazzi; Roberto D'Ambra, both of Milan; Roberto Di Cintio; Carlo Rescalli, both of S.Donato Milanese; Alessandro Vetere, Milan, all of Italy

[73] Assignee: Snamprogetti, S.p.A., Milan, Italy

[*] Notice: The portion of the term of this patent subsequent to Dec. 31, 2002 has been disclaimed.

[21] Appl. No.: 565,459

[22] Filed: Dec. 27, 1983

[30] Foreign Application Priority Data

Jan. 19, 1983 [IT] Italy .............................. 19177 A/83

[51] Int. Cl.⁴ .............................................. F25J 3/02
[52] U.S. Cl. ......................................... 62/17; 55/68; 55/73; 62/20
[58] Field of Search ................... 62/17, 20; 55/68, 73; 48/196 R; 208/189, 207, 208 R, 236, 347, 350, 351, 354, 355

[56] References Cited

U.S. PATENT DOCUMENTS 4,097,250 6/1978 Pagani et al. .
4,305,733 12/1981 Scholz et al. ........................... 62/17

Primary Examiner—Frank Sever
Attorney, Agent, or Firm—Morgan, Finnegan, Pine, Foley & Lee

[57] ABSTRACT

A process for removing acid gases from natural or synthesis gases by absorption, comprising the following stages:
(a) cooling the natural or synthesis gas to be purified to condense part of the $CO_2$ contained in said gas;
(b) feeding the cooled and partly condensed gas to an absorption column in order to reduce the acid gas content to the required value;
(c) regenerating the solvent or solvents used in the acid gas absorption, the solvent or solvents used being chosen from esters, alcohols and ethers of low molecular weight.

45 Claims, 3 Drawing Figures

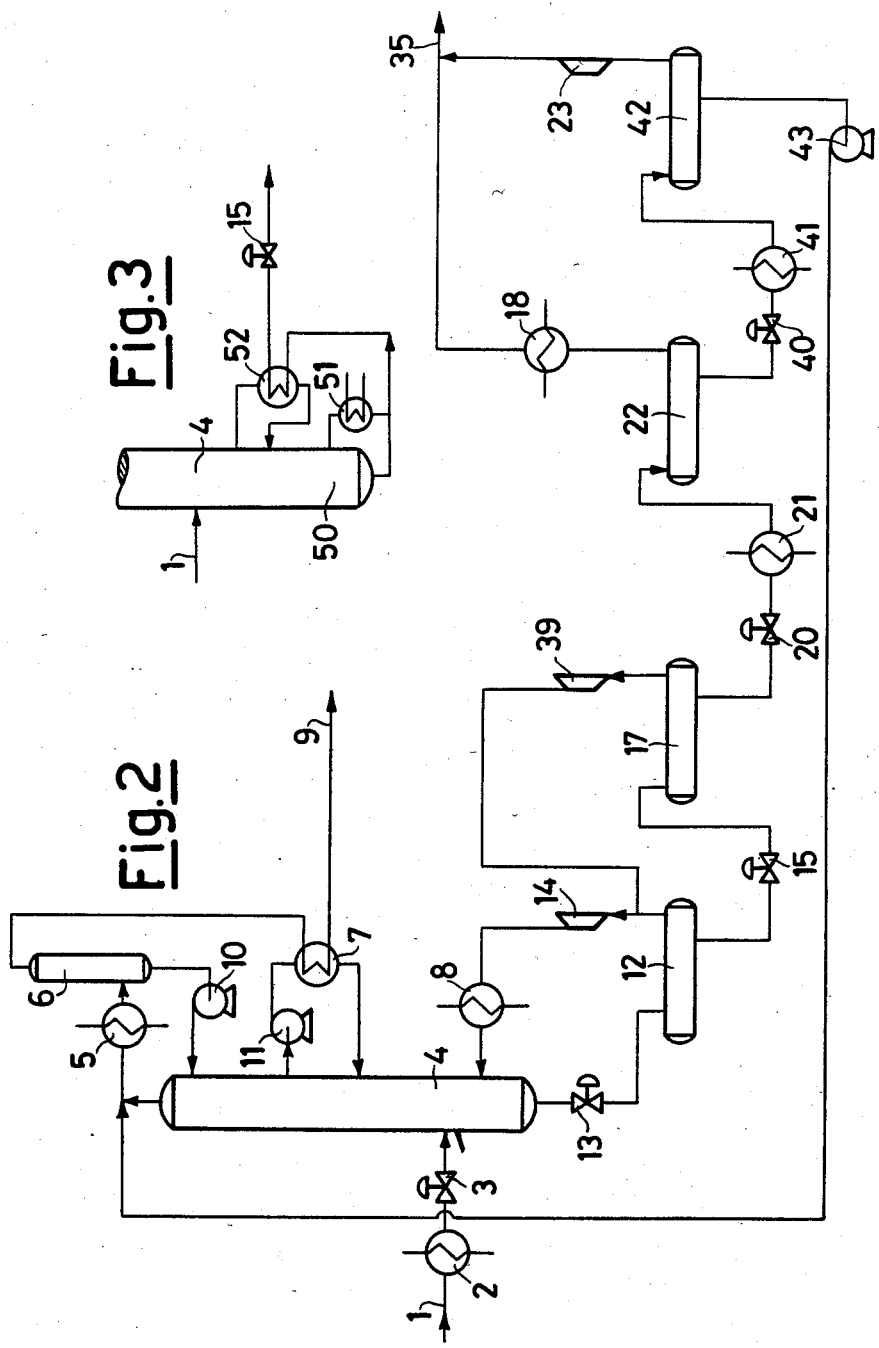

CRYOGENIC PROCESS FOR REMOVING ACID GASES FROM GAS MIXTURES BY MEANS OF A SOLVENT

This invention relates to a process for removing acid gases such as hydrogen sulphide and carbon dioxide from gas mixtures which contain them, which is particularly suitable for treating gaseous mixures having even very high acid gas contents.

The processes of the known art for solving this problem are technically suitable for treating gases which when in their crude state contain only relatively small percentages of acid gases.

This is because they were developed during a period in which energy costs were relatively low, and thus only natural gases having low quantities of such components were exploited.

Such processes of the known art can also be used for treating gases of high acid component content, but the economical consequences and in the limit also the technical consequences are unacceptable. This is because such processes are based essentially on absorption by means of selective solvents which retain the acid components and thus leave the gas purified.

The treatment cost is therefore to a good approximation proportional to the solvent quantity used as a proportion of the gas quantity to be treated. This solvent quantity increases with the content of acid components.

The purified gas must thus bear the treatment cost.

It is therefore apparent that the cost of the treatment according to the known art rises in an unacceptable manner as the acid gas content increases.

In the current energy situation, the use of the available resources must be optimised.

For the exploitation of gas fields of high acid gas content or for purifying synthesis gases produced from fuel oil or coal there is therefore a need for treatment processes suitable for gases of high and very high acid component content able to provide products within a very tight specification.

The treatment of such gases requires the use of mixed cryogenic and solvent methods so as to combine the advantages of the two technologies, in order to obtain good gas purification at acceptable cost.

The present applicant has already patented a process of this type in U.S. Pat. No. 4,097,250 of June 6, 1979. This patent describes the purification of a crude gas containing more than 70% of acid gases by the combined use of low-temperature distillation and solvent absorption. The described solvents are dimethylether-polyethylene glycol and propylene carbonate.

A new purification process has now been discovered, which is particularly suitable for treating gases of high acid gas content, and which uses a class of selective solvents particularly suitable for purification in a cryogenic cycle.

The subject matter of the present invention is the use of such solvents in the treatment cycle described hereinafter.

The solvents of the process according to the invention are substantially low molecular weight esters, alcohols and ethers of the following classes:

Alcohol esters of general formula $R_1COOR_2$ where $R_1$ and $R_2$ indicate alkyl groups of 1 to 4 carbon atoms, which can be the same or different, in which one or more hydrogen atoms can be substituted by alcohol groups, such as methyl formate, methyl acetate, ethyl acetate or monoethylene glycol acetate.

Glycol esters of general formula

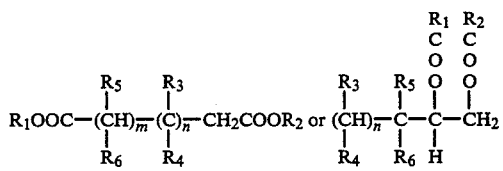

where $R_1$ and $R_2$, which can be the same or different, indicate alkyl groups of 1 to 4 carbon atoms, $R_3$, $R_4$, $R_5$, $R_6$, which can be the same or different, indicate either alkyl groups of 1 to 3 carbon atoms or hydrogen atoms, and m and n are whole numbers which can assume the value 0 or 1, examples being 1,3-propanediol diacetate, 2,2-dimethyl-1,3-propanediol diacetate, 1,2-propanediol diacetate and monoethylene glycol diacetate.

Cyclic esters (lactones) of formula

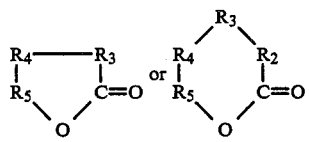

in which $R_2$, $R_3$, $R_4$, $R_5$, which can be the same or different, are alkylene groups in which one or more hydrogen atoms can also be substituted by alkyl, alcohol or ether groups, examples being butyrolactone and caprolactone.

Alcohols of general formula

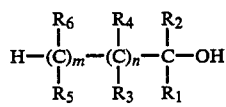

in which $R_1$, $R_2$, $R_3$, $R_4$, $R_5$ and $R_6$, which can be the same or different, are either alkyl groups of 1 to 3 carbon atoms or hydroxyl groups or hydrogen atoms, and m and n are whole numbers which can assume the value 0 or 1, examples being monoethylene glycol, diethylene glycol, 1,2-propanediol, 1,4-butanediol, methanol, ethanol, propanol, isopropanol, n-butanol, isobutanol, sec-butanol, tert-butanol and 1,3-propanediol.

Cyclic ethers such as

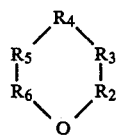

in which $R_2$, $R_5$, $R_6$, which can be the same or different, are alkylene groups in which the hydrogen can also be substituted by alkyl or methoxy groups, $R_3$ can be an oxygen atom or an alkylene group in which the hydrogen can also be substituted by alkyl or methoxy groups, $R_4$ can be as $R_3$, or can be lacking in the case of a five atom ring, examples being tetrahydrofuran, methyl tetrahydrofuran, tetrahydropyran, 1,3-dioxolane, 2-methoxy-1,3-dioxolane and 1,4-dioxane.

Ethers of general formula $$R_1-O-CH_2-(R_3)_n-CH_2-O-R_2$$

where $R_1$ indicates an alkyl group of 1 to 4 carbon atoms, $R_2$ indicates either an alkyl group of 1 to 4 carbon atoms or a hydrogen atom, $R_3$ is either an alkylene group or $(CH_2-O-CH_2)$, and n is a whole number which can assume the value 0 or 1, examples being 1,2-dimethoxyethane, 1,2-methoxyethoxyethane, dimethoxydiethylene glycol and monomethoxydiethylene glycol.

Ethers of general formula $R_1-O-R_2$, where $R_1$ and $R_2$, which can be the same or different, are alkyl groups of 1 to 4 carbon atoms in which one or more hydrogen atoms can be substituted by alcohol groups, examples being ethyl ether, propyl ether, 1-methoxyethanol, 1-methoxy-2-propanol, 1-methoxy-3-propanol and ethoxyethanol.

Ester-ethers, ie compounds containing both the functions, of formula:

$$(R_4-O)_n-R_1-COOR_2(OR_3)_m$$

where $R_3$ and $R_4$, which can be the same or different, indicate alkyl groups of 1 to 4 carbon atoms, $R_2$ indicates an alkylene or alkyl group of 1 to 4 carbon atoms, $R_1$ is the same as either $R_2$ or $R_3$, and m and n are whole numbers which can assume the value 0 or 1, examples being 2-methoxyethyl acetate, methylmethoxy acetate and ethylmethoxy acetate.

The aforesaid solvents combine various properties particularly favorable for their use as selective solvents.

In this respect, they have high stability under the conditions in which they are used, high solvent power towards acid gases, high selectivity for $H_2S$ and $CO_2$ towards hydrocarbons, low molecular weight and a low melting point. This latter characteristic is essential for their application in a cryogenic process. In the case of natural gas treatment, after low-temperature condensation and before final absorption with solvent, the gas is available at a low temperature substantially less than 0° C.

During final absorption, it is useful to be able to reach a temperature considerably lower than the gas temperature, that which is very favorable in that it increases the absorbent capacity of the solvent and its selectivity.

Said solvents in the process of this invention have a low melting point and are thus particularly suitable for being used in a cryogenic process.

The solvents according to the invention can be used either alone or in mixture, with suitable additions of water and/or of an organic compound of low melting point and/or low viscosity and/or low molecular weight, such as dimethylether, methanol, acetone, toluene, ethanol, propane, butane or pentane, in order to adjust the solvent characteristics as a function of the gas to be treated and its pressure and temperature conditions.

The organic compound can be added in the proportion of between 0.3 and 40% by weight of the resultant mixture, and the water up to a maximum of 10% by weight.

The process according to the invention consists of the following operations:

(a) cooling the natural or synthesis gas to be purified to condense part of the acid gases contained in said gas;

(b) feeding the cooled and partly condensed gas to an absorption column in order to reduce the acid gas content to the required value;

(c) regenerating the solvent or solvents used in the acid gas absorption.

The natural or synthesis gas can be cooled under point (a) in a heat exchanger by vaporising part of the acid gases contained in the $CO_2$-rich solvent at a suitable point of the regeneration process. It is preferable for the acid gases which remain uncondensed after cooling under point (a) to not exceed 30 mol% in the gaseous phase, and more preferably to lie between 15 and 30 mol%.

The gas cooling can also take place inside the absorption column. Such cooling, which condenses part of the acid gases, means that the distillation column used in previous processes can be dispensed with.

The solvent or solvents used for acid gas absorption in the absorption column can be initially regenerated by one or more expansion stages (3 at most) from which mainly the useful components co-absorbed in stage (b) are recovered, then by a further expansion stage or stages (4 at most) from which mainly acid gases are evolved. The solvents regenerated in this manner are recycled to the absorption column.

Solvent regeneration can be completed by a distillation column if $H_2S$ is contained in the acid gases, as the specifications for residual $H_2S$ in the treated gas are much stricter than for $CO_2$ alone. If the acid gases contain $CO_2$, the use or otherwise of a regenerating distillation column depends on the maximum allowable $CO_2$ value in the purified gas.

If the regeneration column is present, part of the solvent leaving the expansion stages can be fed to the regeneration column, whereas the remaining part, not completely regenerated, can be recycled to the absorption column.

The useful components evolved during the acid gas-rich solvent expansion stages are compressed, cooled and recycled to the absorption column.

The acid gas-rich solvent can be expanded through valves or, at least partly, in turbines.

The regeneration of the acid gas-rich solvent by expansion can be supplemented by heating said solvent in order to favor acid gas removal by vaporisation and to recover cold for use in the process. The number of expansion stages from which mainly acid gases are evolved can be between 1 and 4, to produce acid gas streams at decreasing pressure, of which one or two can be kept under vacuum, in which case the acid gases evolved must be recompressed. However, in some cases it is not necessary to go below atmospheric pressure because the final pressure is a function of the temperature attained and of the purification required.

The streams containing mainly acid gases produced at high pressure can be expanded through valves or by turbines down to their required delivery pressure in order to produce work and cold.

The absorption column operates at a pressure of between 20 and 110 kg/cm$^2$ and at a temperature of between $-100°$ and 10° C. If the distillation column for solvent regeneration is present, said column operates at a pressure of between 0.1 and 5 kg/cm$^2$, at an overhead temperature of between $-60°$ and 10° C., and at a bottom temperature of between 10° and 200° C.

A further step consists of adding solvent to the natural or synthesis gas to be purified before being cooled by heat exchangers or by expansion through valves or turbines in order to prevent CO$_2$ crystallisation.

The absorption column solvent can be withdrawn from an intermediate point of said absorption column, cooled using at least part of the residual cold of the treated gas and/or at least part of the residual cold of the acid gases, and fed to the column immediately below its withdrawal point.

The exhausted solvent from the absorption column can be mixed with the natural or synthesis gas and cooled in order to effect preliminary absorption and reduce the load on the absorber.

If the process also comprises the distillation regeneration column, the regenerated solvent from the distillation column can be mixed with the gas leaving the absorption column and cooled in a heat exchanger before being fed to the absorption column.

The invention is described hereinafter with reference to the flow diagram of the accompanying FIG. 1, which represents a preferred embodiment but must not be considered limitative of the invention.

The crude gas reaches the plant through the pipe 1, is cooled in 2 and expanded through the valve 3, and is washed in counter-current with the solvent in the absorber 4 in order to remove the acid gas.

The gas leaving the absorber is mixed with completely purified solvent and cooled in the heat exchanger 5, separated from the solvent in 6 and fed for cold recovery to the heat exchangers 7 and 8, and then to the main by way of the pipe 9. The cooled solvent, separated from the gas in 6, is pumped into the absorber 4 by the pump 10. Further solvent, not completely purified, is fed into the absorber at intermediate height. In order to lower the average absorption temperature, the solvent is extracted from an intermediate plate of the absorber, pumped by 11 and cooled by the treated gas in 7.

The acid gas-rich solvent leaving the absorber 4 is regenerated by expansion. It is fed to the separator 12 through the valve 13, in which a methane-rich gas evolves and is recycled to the absorber 4 by the compressor 14 after cooling against the treated gas in 8. The solvent leaving 12 is expanded through the valve 15, cooled in 16 and fed to the separator 17, from which acid gases evolve. They are heated in 18 and 19 and discharged from the plant.

The solvent leaving 17 is expanded under vacuum through the valve 20, heated in the heat exchanger 21 and then fed to the separator 22, from which acid gases are evolved, these being compressed to approximately atmospheric pressure by the compressor 23 and discharged from the plant.

Part of the solvent leaving 22, which is not yet completely purified, is fed by the pump 24 and through the valve 25 to the absorber 4 at an intermediate height (26).

The remainder of the solvent is fed by the pump 27 through the valve 28 to the regeneration column 29 after being heated in 30. The solvent is stripped of the acid gases in the regenerator 29, which is provided with a condenser 31, reflux accumulator 32, reflux pumps 33 and reboiler 34. This latter is heated by any heat source.

The acid gases leaving 32 are added to those from the heat exchangers 18 and 19 and to those from the compressor 23. They are then discharged through the pipe 35.

The regenerated solvent is cooled by external cooling means (air or water and/or a suitable refrigeration cycle) in 36 and by the solvent to be regenerated in 30, and is fed by the pump 37 to the cooler 5 after being cooled in the heat exchanger 38.

An example is given hereinafter with reference to FIG. 2, its purpose being to better illustrate the invention but without in any way being considered as limitative of the invention itself.

EXAMPLE

The crude inlet gas (1) has a throughput of 629 mol/h and is at −9° C. and 63 ata. Its molar composition is as follows:

| | |
|---|---|
| $N_2$ | 11.10% |
| $C_1$ | 36.92% |
| $C_2$ | 1.84% |
| $C_3$ | 0.79% |
| $C_4$ | 0.13% |
| $CO_2$ | 49.22% |
| | 100.00% |

The crude gas is cooled to −38.6° C. in the heat exchanger 2, expanded through the valve 3 to 42.5 ata to attain a temperature of −49.5° C., and fed to the absorber 4.

The solvent used is a slightly perfumed ester with a pleasant fruity taste, namely methyl acetate.

The gas leaves the top of the absorber, is mixed with 126 moles of regenerated methyl acetate containing 7 mol% of $CO_2$ and is cooled in 5° to −76° C.

The mixture of solvent and gas is separated in 6, from which the gas leaves containing 1 mol% of $CO_2$. After recovering cold in 7, the treated gas is discharged from the plant through the pipe 9. The solvent is pumped to the absorber by the pump 10. The solvent is withdrawn from an intermediate point of the column, cooled in 7 against the cold of the treated gas and is reintroduced by the pump 11 into the column immediately below the point from which it is withdrawn. The rich solvent leaving the absorber at −26° C. is expanded in two stages through the valves 13 and 15 into the two separators 12 and 17, of which the respective conditions are 20 ata, −36° C. and 8.5 ata, −47° C. The vapours are compressed in the two compression stages 14 and 39, cooled in 8° to −16° C. and recycled to the absorber.

The solvent leaving the separator 17, the methane content of which is reduced to 4.9 moles, is expanded to 1.3 ata in 20 and heated in 21° to −64° C. The heat exchanger 21 and the heat exchanger 2 are the same heat exchanger.

The $CO_2$ which vaporises is separated in 22, heated in 18 and discharged from the plant (35).

The solvent leaving 22 is expanded in 40 to 0.4 ata and heated in 41° to −53° C. The vaporised $CO_2$ is separated in 42 and compressed in 23 to the pressure of the $CO_2$ discharge manifold. The regenerated solvent is recycled to the absorber by means of the pump 43. Another method for recovering the useful co-absorbed products is shown in FIG. 3. The rich solvent leaving the absorber 4 is directly fed to an exhaustion section 50 lying below the absorber 4. Heat is administered to the exhaustion section by suitable heating fluids in the bottom reboiler 51 and in the intermediate reboiler 52. The column bottom product is cooled in this latter and now contains only negligible quantities of useful compounds. It is expanded through the valve 15 and fed to the separator 17. The new plant items 50, 51 and 52 replace the plant items 13, 12 and 14 of FIGS. 1 and 2.

We claim:

1. A process for removing acid gases from natural or synthesis gases comprising recovering a product which is essentially acid gas free from a feed material of natural or synthesis gases containing about 50 mole % or more of acid gases by the following steps:
   (a) cooling the natural or synthesis gas to be purified sufficiently to condense part of the acid gases contained in said gas so that the acid gases which remain uncondensed do not exceed 30 mole % in the gaseous phase;
   (b) selectively removing acid gases which remain uncondensed from the cooled and partly condensed gas in an absorption column with at least one regeneratable solvent having a high selectivity for said acid gases in order to produce said essentially acid gas free product; and
   (c) regenerating the solvent or solvents used in the acid gas absorption;
   the solvent used being selected from the group consisting of low molecular weight esters, alcohols and ethers.

2. The process of claim 1 wherein said solvent comprises an alcohol ester having the formula:

$$R_1COOR_2,$$

wherein:
  $R_1$ and $R_2$ represent, independently or simultaneously, $C_1$–$C_4$ alkyl in which one or more hydrogen atoms can be substituted by an alcohol group.

3. The process of claim 2, wherein the selective solvent is methylformate, methylacetate, ethylacetate or monoetheleneglycol acetate.

4. The process of claim 1 wherein said solvent comprises a glycol ester having a formula

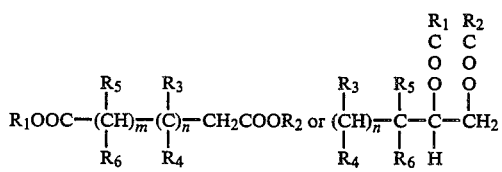

wherein:
  $R_1$ and $R_2$, which can be the same or different, represent alkyl groups having 1 to 4 carbon atoms;
  $R_3$, $R_4$, $R_5$ and $R_6$ represent, independently or simultaneously, $C_1$–$C_3$ alkyl or —H; and
  m and n are 0 or 1.

5. The process of claim 4, wherein the selective solvent is 1,3-propanediol diacetate, 2,2-dimethyl-1,3-propanediol diacetate, 1,2-propanediol diacetate or monoethyleneglycol diacetate.

6. The process of claim 1 wherein said solvent comprises a cyclic ether having a formula

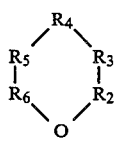

wherein:
  $R_2$, $R_5$ and $R_6$ represent, simultaneously or independently, alkylene groups in which one or more of the hydrogens can be substituted by alkyl or methoxy groups;
  $R_3$ represents —O— or an alkylene group in which the hydrogens can be substituted by alkyl or methoxy groups; and
  $R_4$ is equal to $R_3$ or is absent in the case of a five member ring.

7. The process of claim 6, wherein the selective solvent is tetrahydropyran, 1,3-dioxolane, 1,4-dioxane, tetrahydrofuran, methyltetrahydrofuran, or 2-methoxy-1,3-dioxolane.

8. The process of claim 1 wherein said solvent comprises an ether having the formula:

$$R_1\text{—O—}CH_2\text{—}(R_3)n\text{—}CH_2\text{—O—}R_2,$$

wherein:
  $R_1$ represents $C_1$–$C_4$ alkyl;
  $R_2$ represents —H or $C_1$–$C_4$ alkyl;
  $R_3$ represents an alkylene group or —CH$_2$—O—CH$_2$—; and
  n is 0 or 1.

9. The process of claim 8, wherein the selective solvent is 1,2-dimethoxyethane, 1,2-methoxyethoxyethane, dimethoxydiethylene glycol or monomethoxydiethylene glycol.

10. The process of claim 1 wherein said solvent comprises an alcohol having the formula

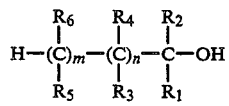

wherein:
  $R_1$, $R_2$, $R_3$, $R_4$, $R_5$ and $R_6$ represent, simultaneously or independently, $C_1$–$C_3$ alkyl, —OH or —H; and
  m and n are 0 or 1.

11. The process of claim 10, wherein the selective solvent is monoethylene glycol, diethylene glycol, 1,2-propanediol, 1,3-propanediol, 1,4-butanediol, methanol, ethanol, propanol, isopropanol, n-butanol, isobutanol, sec-butanol or tert-butanol.

12. The process of claim 1 wherein said solvent comprises a cyclic ester (lactone) having the formula

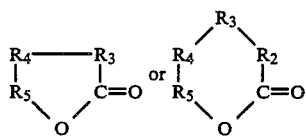

wherein:
  $R_2$, $R_3$, $R_4$ and $R_5$ represent, simultaneously or independently, alkylene groups in which one or more hydrogen atoms can be substituted by alkyl, alcohol or ether groups.

13. The process of claim 12 wherein the selective solvent is butyrolactone or caprolactone.

14. The process of claim 1 wherein said solvent comprises an ether having the formula $$R_1\text{—O—}R_2$$

wherein:
  $R_1$ and $R_2$ represent, simultaneously or independently, $C_1$–$C_4$ alkyl in which one or more hydrogen can be substituted by an alcohol group.

15. The process of claim 14, wherein the selective solvent is 1-methoxyethanol, 1-methoxy-2-propanol, 1-methoxy-3-propanol, ethoxyethanol, ethyl ester or propyl ether.

16. The process of claim 1 wherein said solvent comprises an ester-ether having the formula $$(R_4-O)_n-R_1-COOR_2(OR_3)_m$$

wherein:
$R_3$ and $R_4$ represent, simultaneously or independently, $C_1-C_4$ alkyl:
$R_2$ represents $C_1-C_4$ alkylene or alkyl;
$R_1$ represents the same $R_2$ or $R_3$; and
m and n are 0 or 1.

17. The process of claim 16, wherein the selective solvent is 2-methoxyethyl acetate, methylmethoxy acetate or ethylmethoxy acetate.

18. The process of claim 1, wherein the solvent used for the acid gas absorption in the absorption column is regenerated initially by one or more expansion stages from which mainly the useful components co-absorbed in stage (b) are recovered, followed by at least one further expansion stage from which mainly acid gases are evolved, the regenerated solvent then being recycled to the absorption column.

19. The process of claim 18, wherein the solvent regeneration is completed by a distillation column.

20. The process of claim 19, wherein part of the solvent leaving the expansion stages is fed to the distillation column, the remainder being recycled to the absorption column.

21. The process of claim 19, wherein the acid gas rich solvent is expanded through valves or, at least partly, in turbines.

22. The process of claim 18, wherein expansion stages from which the mainly useful components coabsorbed in stage (b) are recovered can be from 1 to 3 in number.

23. The process of claim 18, wherein the expansion stages from which the mainly acid gases evolve can be from 1 to 4 in number, to produce streams at decreasing pressures.

24. The process of claim 23, wherein one or two expansion stages are kept under vacuum.

25. The process of claim 23, wherein the stream or streams containing mainly acid gases produced at high pressure are expanded to their delivery pressure in turbines in order to produce work and refrigeration.

26. The process of claim 18, wherein the regeneration of the acid gas-rich solvent by expansion is supplemented by heating said solvent in order to favor acid gas removal by vaporization and to recover cold for use in the process.

27. The process of claim 18, wherein the useful components which evolve during the acid gas-rich solvent expansion stage or stages are compressed, cooled and recycled to the absorption column.

28. The process of claim 19, wherein said distillation column for solvent regeneration operates at a pressure between 0.1 and 5 kg/cm², at an overhead temperature of between −60° and 10° C., and at a bottom temperature of between 10° and 200° C.

29. The process of claim 1, wherein solvent is added to the natural or synthesis gas from the first absorption column before being cooled by heat exchange or by expansion through valves or in turbines in order to prevent $CO_2$ crystallization.

30. The process of claim 1, wherein the solvent used in the absorption column of stage (b) is withdrawn from an intermediate point of said absorption column, cooled and reintroduced into the column immediately at a point below the withdrawal point.

31. The process of claim 30, wherein at least part of the intermediate cooling of the solvent is carried out using at least part of the residual cold of the treated gas.

32. The process of claim 30, wherein at least part of the intermediate cooling of the solvent is carried out using at least part of the residual cold of the $CO_2$.

33. The process of claim 1, wherein the exhausted solvent leaving the absorption column is mixed with the natural or synthesis gas amd then cooled.

34. The process of claim 1, wherein the regenerated solvent is mixed with the gas leaving the absorption column and cooled in a heat exchanger before being fed to the absorption column.

35. The process of claim 1, wherein the gas to be purified is cooled in the first stage by means of a heat exchanger by vaporizing part of the $CO_2$ contained in the $CO_2$-rich solvent at an intermediate point of the solvent regeneration.

36. The process of claim 1, wherein the cooling in the first stage is effected inside the absorption column.

37. The process of claim 1, wherein the exhausted solvent leaving the absorption column is fed to an exhaustion section provided with a reboiler in which the useful components are stripped off and fed to the absorption column.

38. The process of claim 1, wherein the bottom product of the exhaustion section is sub-cooled in an intermediate reboiler of said exhaustion section.

39. The process of claim 37 or 38, wherein the heat exchanger which cools the overhead product gas leaving the absorption column in mixture with the regenerated solvent uses the cold available by vaporizing the $CO_2$ contained in the exhausted solvent.

40. The process of claim 1, wherein water and/or an organic compound of low melting point and/or low viscosity and/or low molecular weight are added to the selective solvent or solvents.

41. The process of claim 40 wherein the organic compound is added in the proportion of between 0.3 and 40% by weight of the resultant mixture, and the water is added up to a maximum of 10% by weight.

42. The process of claim 40, wherein the organic compound is methanol, ethanol, dimethylether, acetone, propane, butane, pentane, toluene, hexane, either alone or in admixture.

43. The process of claim 1 wherein the gas mixture is cooled by expansion or heat exchange.

44. The process of claim 1 wherein in said stage (a), the acid gases which remain uncondensed do not exceed 15 mole %.

45. The process of claim 1, wherein the absorption column of stage (b) operates at a pressure of between 20 and 110 kg/cm² and at a temperature of between −100° and 10° C.

* * * * *